(12) United States Patent
Privitera

(10) Patent No.: US 11,801,368 B2
(45) Date of Patent: Oct. 31, 2023

(54) GUIDEWIRE

(71) Applicant: C.R. Bard, Inc., Murray Hill, NJ (US)

(72) Inventor: Salvatore Privitera, Mason, OH (US)

(73) Assignee: C.R. Bard, Inc., Murray Hill, NJ (US)

(*) Notice: Subject to any disclaimer, the term of this patent is extended or adjusted under 35 U.S.C. 154(b) by 1202 days.

(21) Appl. No.: 15/604,949

(22) Filed: May 25, 2017

(65) Prior Publication Data

US 2018/0339138 A1    Nov. 29, 2018

(51) Int. Cl.
*A61M 25/09* (2006.01)

(52) U.S. Cl.
CPC ... *A61M 25/09* (2013.01); *A61M 2025/09083* (2013.01); *A61M 2025/09108* (2013.01); *A61M 2025/09133* (2013.01); *A61M 2025/09166* (2013.01)

(58) Field of Classification Search
None
See application file for complete search history.

(56) References Cited

U.S. PATENT DOCUMENTS

| | | | | |
|---|---|---|---|---|
| 5,229,211 A | * | 7/1993 | Murayama | A61L 29/085 |
| | | | | 428/424.4 |
| 5,465,733 A | * | 11/1995 | Hinohara | A61M 25/09 |
| | | | | 600/585 |
| 5,797,857 A | | 8/1998 | Obitsu | |
| 5,876,356 A | * | 3/1999 | Viera | A61L 31/022 |
| | | | | 600/585 |
| 6,013,855 A | * | 1/2000 | McPherson | A61L 27/34 |
| | | | | 427/2.24 |
| 6,306,105 B1 | * | 10/2001 | Rooney | A61M 25/09 |
| | | | | 600/585 |
| 7,115,101 B2 | | 10/2006 | Cornelius et al. | |
| 2002/0019599 A1 | | 2/2002 | Rooney et al. | |
| 2002/0038131 A1 | | 3/2002 | Burmeister et al. | |
| 2002/0193706 A1 | | 12/2002 | Ferrera | |
| 2004/0122145 A1 | * | 6/2004 | Klosowski | C08K 5/10 |
| | | | | 524/284 |
| 2004/0127616 A1 | * | 7/2004 | Wentworth | C08K 5/10 |
| | | | | 524/284 |

(Continued)

FOREIGN PATENT DOCUMENTS

| | | |
|---|---|---|
| CN | 102205165 | 10/2011 |
| EP | 2371402 | 10/2011 |

(Continued)

OTHER PUBLICATIONS

Japan Patent Office, Notice of Reasons for Rejection in JP 2019-564888, dated Aug. 2, 2021.

(Continued)

*Primary Examiner* — Jay B Shah
(74) *Attorney, Agent, or Firm* — Dorton & Willis LLP; Ryan Willis

(57) ABSTRACT

A guidewire comprising a hydrophilic surface coating encasing a core and a metal coil along a longitudinal length of the hydrophilic surface coating to form a distal closed tip, the metal coil circumscribing the core along a predetermined length, the core extending longitudinally beyond the metal coil in both a proximal direction and a distal direction, wherein a proximal section of the guidewire includes a hydrophobic surface coating.

39 Claims, 8 Drawing Sheets

(56) References Cited

U.S. PATENT DOCUMENTS

| | | | |
|---|---|---|---|
| 2004/0167603 A1* | 8/2004 | Jackson | A61F 2/91 623/1.12 |
| 2004/0176502 A1* | 9/2004 | Raymond | C04B 41/009 523/416 |
| 2005/0065456 A1 | 3/2005 | Eskuri | |
| 2005/0075582 A1* | 4/2005 | Cornelius | A61L 31/10 600/585 |
| 2005/0244459 A1* | 11/2005 | DeWitt | A61L 29/085 424/426 |
| 2006/0121218 A1 | 6/2006 | Obara et al. | |
| 2007/0293791 A1* | 12/2007 | Lee | A61L 31/10 600/585 |
| 2008/0146967 A1* | 6/2008 | Richardson | A61L 31/18 600/585 |
| 2010/0049165 A1* | 2/2010 | Sutherland | A61M 25/0069 604/508 |
| 2011/0178436 A1* | 7/2011 | Maki | A61M 25/09 600/585 |
| 2011/0230862 A1 | 9/2011 | Segner et al. | |
| 2011/0245730 A1 | 10/2011 | Satozaki | |
| 2012/0065622 A1* | 3/2012 | Cornish | A61M 25/09 604/528 |
| 2013/0292365 A1* | 11/2013 | Cornish | A61M 25/09 219/121.72 |
| 2015/0182673 A1 | 7/2015 | Delaney, Jr. et al. | |
| 2017/0291013 A1 | 10/2017 | Pereira et al. | |

FOREIGN PATENT DOCUMENTS

| | | |
|---|---|---|
| JP | H07-227429 | 8/1995 |
| JP | 2000-509641 | 8/2000 |
| JP | 2002-514474 | 5/2002 |
| JP | 2003-513764 | 4/2003 |
| JP | 2005-348919 | 12/2005 |
| JP | 4118069 B2 * | 7/2008 |
| JP | 2009-112373 | 5/2009 |
| JP | 2013-192914 | 9/2013 |
| WO | 98/39049 | 9/1998 |
| WO | 99/58183 | 11/1999 |
| WO | 01/36034 | 5/2001 |
| WO | 2005/120625 | 12/2005 |
| WO | PCT/US18/33583 | 8/2018 |

OTHER PUBLICATIONS

Japan Patent Office, Notice of Reasons for Rejection in JP 2019-564888, dated Nov. 24, 2020.
European Patent Office, Extended European Search Report in EP 18806417.4, dated Feb. 15, 2021.
National Intellectual Property Administration, P.R. China, First Office Action in CN 201880033981.6, dated Apr. 30, 2021.

* cited by examiner

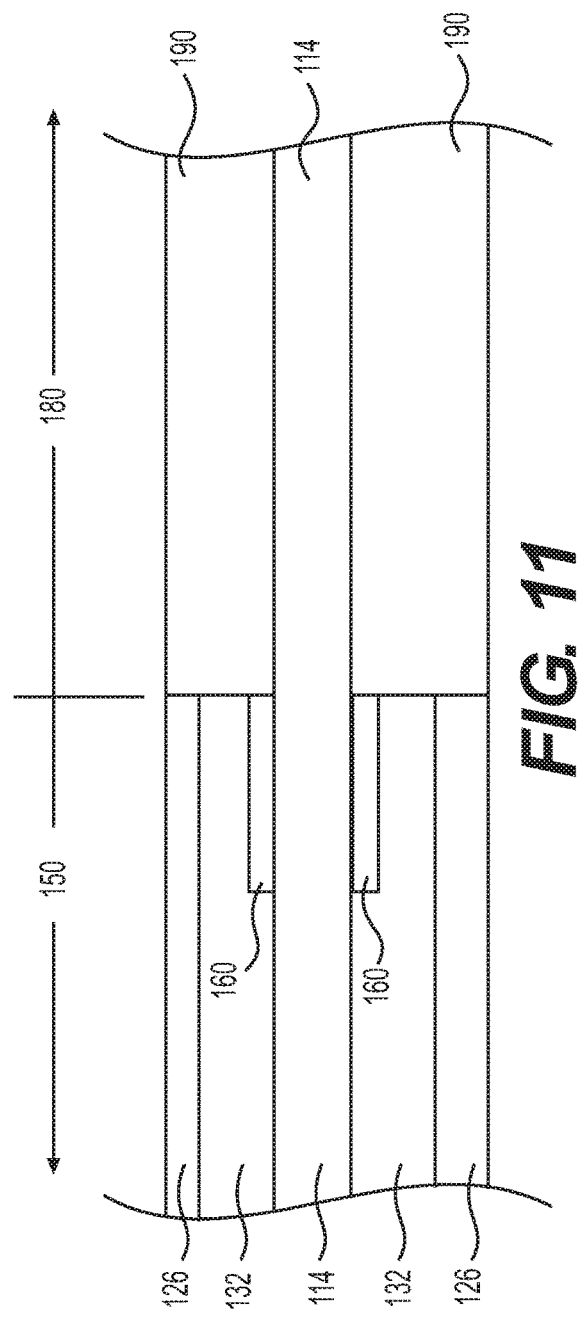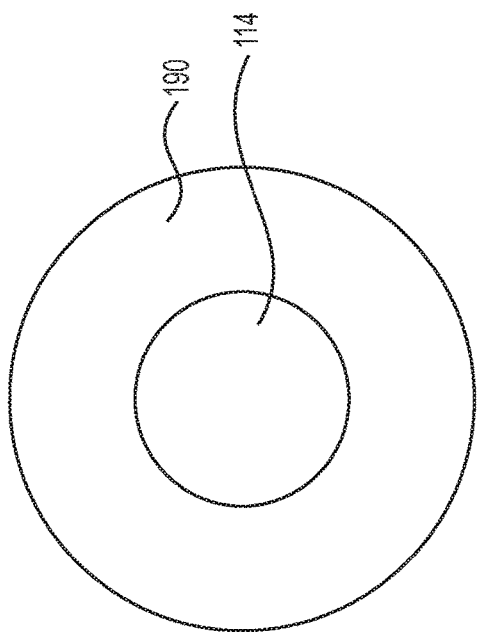

GUIDEWIRE

INTRODUCTION TO THE INVENTION

The present disclosure is directed to guidewires, as well as method of fabricating and use the same. Guidewires are used in the art for accessing and navigating tortuous bodily lumens as part of a medical procedure. For example, a guidewire may be used to access and navigate urinary tracts. After arriving at the intended location within the body lumen, further surgical device may be inserted in to the lumen using the guidewire as a track along which the further surgical device slides. However, it has been discovered that there is a need in the art for a guidewire that more easily navigates tortuous bodily lumens and allows surgical devices to slide thereover more easily (i.e. with less friction between the device and the guidewire) while providing tactility to the user to allow adequate control and placement of the guidewire within the bodily lumen.

Embodiments of the instant disclosure address a weakness of both industry standard guidewire types to provide both tactile feedback and easy device passage. No currently available guidewire provides both of these features. Rather, hybrid guidewires offer improved tactile feedback to increase control and positioning accuracy within the bodily lumen, but do not allow for easy passage of surgical devices thereover. On the other hand, hydrophilic guidewires offer easy passage of surgical devices thereover, but lack tactile feedback. Consequently, the embodiments of the instant disclosure address a need in the art currently unmet.

It is a first aspect of the present invention to provide a guidewire comprising a hydrophilic surface coating encasing a core and a metal coil along a longitudinal length of the hydrophilic surface coating to form a distal closed tip, the metal coil circumscribing the core along a predetermined length, the core extending longitudinally beyond the metal coil in both a proximal direction and a distal direction, where a proximal section of the guidewire includes a hydrophobic surface coating.

In a more detailed embodiment of the first aspect, at least a portion of the core extending in the distal direction beyond the metal coil includes a silane coating. In yet another more detailed embodiment, the core includes a frustroconical shape that extends beyond the metal coil in the distal direction. In a further detailed embodiment, the silane coating is separated from the hydrophilic surface coating by a thermoplastic polymer layer. In still a further detailed embodiment, the thermoplastic polymer layer is radiopaque. In a more detailed embodiment, the thermoplastic polymer layer comprises a polycaprolactone based polyurethane elastomer. In a more detailed embodiment, the polycaprolactone based polyurethane elastomer comprise tungsten loaded pellethane. In another more detailed embodiment, the core is coated in an epoxy primer. In yet another more detailed embodiment, the epoxy primer comprises a mixture of an epoxy resin, an epoxy polyamine adduct, and a glycidyl ester. In still another more detailed embodiment, the epoxy primer is adjacent the hydrophobic surface coating.

In yet another more detailed embodiment of the first aspect, an overall length of the guidewire is between ten and two hundred inches. In yet another more detailed embodiment, the core has a median diameter between approximately 0.035 inches and 0.038 inches. In a further detailed embodiment, the distal closed tip is atraumatic. In still a further detailed embodiment, the core is at least one of solid and hollowed. In a more detailed embodiment, the core comprises an alloy of nickel, titanium, and cobalt. In a more detailed embodiment, the core includes a cross-sectional shape comprising at least one of circular, oblong, and rectangular. In another more detailed embodiment, the core includes a tapered section. In yet another more detailed embodiment, the core includes a frustroconical section. In still another more detailed embodiment, the guidewire further includes a silane coating interposing the core and the hydrophilic surface coating.

In a more detailed embodiment of the first aspect, the silane coating is spaced from the hydrophilic surface coating by a thermoplastic polymer layer. In yet another more detailed embodiment, the thermoplastic polymer layer is radiopaque. In a further detailed embodiment, the thermoplastic polymer layer comprises a polycaprolactone based polyurethane elastomer. In still a further detailed embodiment, the polycaprolactone based polyurethane elastomer comprise tungsten loaded pellethane. In a more detailed embodiment, the core is coated in an epoxy primer in the form of two ring-shaped coatings spaced apart from one another. In a more detailed embodiment, each of the two ring-shaped coatings is no greater than ten inches in length. In another more detailed embodiment, the metal coil comprises stainless steel. In yet another more detailed embodiment, the metal coil has a radial cross-section that is rectangular in shape.

It is a second aspect of the present invention to provide a guidewire comprising: (a) a first section comprising a core, a hydrophilic layer, and a polymer layer interposing the core and the hydrophilic layer; (b) a second section comprising the core, the hydrophilic layer, and a metal coil interposing the core and the hydrophilic layer; and, (c) a third section comprising the core and a hydrophobic layer, where the hydrophilic layer and the hydrophobic layer comprise an exterior surface of the guidewire; and the hydrophobic layer comprises more than ninety percent of the exterior surface.

It is a third aspect of the present invention to provide a method of fabricating a guidewire comprising: (a) mounting a metal coil over a core so that the metal coil circumscribes the core along a predetermined length, the core extending longitudinally beyond the metal coil in both a proximal direction and a distal direction; (b) encasing the metal coil and a majority of the core in a hydrophilic exterior surface layer so a distal tip of the guidewire is closed; and, (c) forming a hydrophobic exterior surface over a minority of the core.

In a more detailed embodiment of the third aspect, the method further includes shaping the core to create a tapered distal segment. In yet another more detailed embodiment, the method includes shaping the core to create the tapered distal segment include grinding the core to remove material from the core. In a further detailed embodiment, the method includes forming the hydrophobic exterior surface over the minority of the core includes heat shrinking a hydrophobic tube over the minority of the core. In still a further detailed embodiment, the hydrophobic tube is heat shrinked over a proximal-most section of the core. In a more detailed embodiment, the hydrophobic tube comprises polytetrafluoroethylene. In a more detailed embodiment, the method further includes applying an epoxy primer to the core so as to interpose the core and metal coil. In another more detailed embodiment, the epoxy primer is applied to form two rings around the core that are spaced apart from one another. In yet another more detailed embodiment, the method further includes heat treating the applied epoxy primer to bond the core to the metal coil where the epoxy primer was applied.

In still another more detailed embodiment, the method further includes applying a silane primer to a distal most portion of the core.

In yet another more detailed embodiment of the third aspect, the method further includes curing the applied silane primer via a heat treatment. In yet another more detailed embodiment, the method includes encasing the metal coil and a majority of the core in the hydrophilic coating also includes encasing the silane primer.

It is a fourth aspect of the present invention to provide a method of using a guidewire comprising: (a) inserting a closed distal tip of a guidewire into a bodily lumen, the guidewire comprising a hydrophilic surface coating encasing a core and a metal coil along a longitudinal length of the hydrophilic surface coating to form a distal closed tip, the metal coil circumscribing the core along a predetermined length, the core extending longitudinally beyond the metal coil in both a proximal direction and a distal direction, wherein a proximal section of the guidewire includes a hydrophobic surface coating; (b) repositioning the guidewire within the bodily lumen to reach an end location for the closed distal tip while receiving real-time images from a radiation imager that depict a relative location of the distal tip with respect to a section of the bodily lumen; (c) inserting a medical instrument over the guidewire post the distal tip reaching the end location; (d) carrying out a medical procedure using the medical instrument; and, (e) withdrawing the guidewire from the bodily lumen post insertion of the medical instrument.

BRIEF DESCRIPTION OF THE DRAWINGS

FIG. 11 is a longitudinal cross-sectional view of a portion of the third section of the exemplary guidewire of FIG. 1.

FIG. 12 is a radial cross-sectional view of the portion of the third section of the exemplary guidewire of FIG. 1, taken at line E-E.

DETAILED DESCRIPTION

The exemplary embodiments of the present disclosure are described and illustrated below to encompass exemplary guidewires, methods of fabricating the same, as well as methods of using the same. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1:
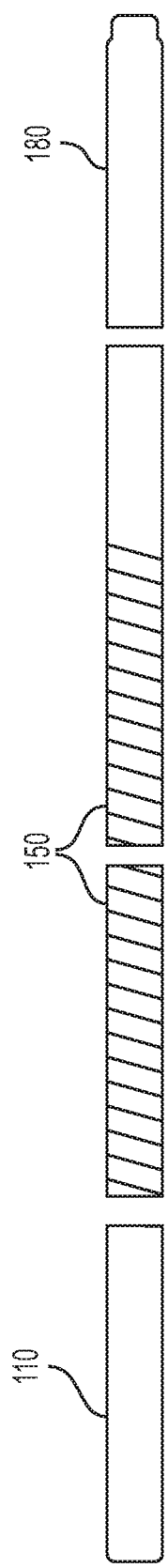
FIG. 1 is an exterior profile view of an exemplary guidewire fabricated in accordance with the instant disclosure.
Figure 2:
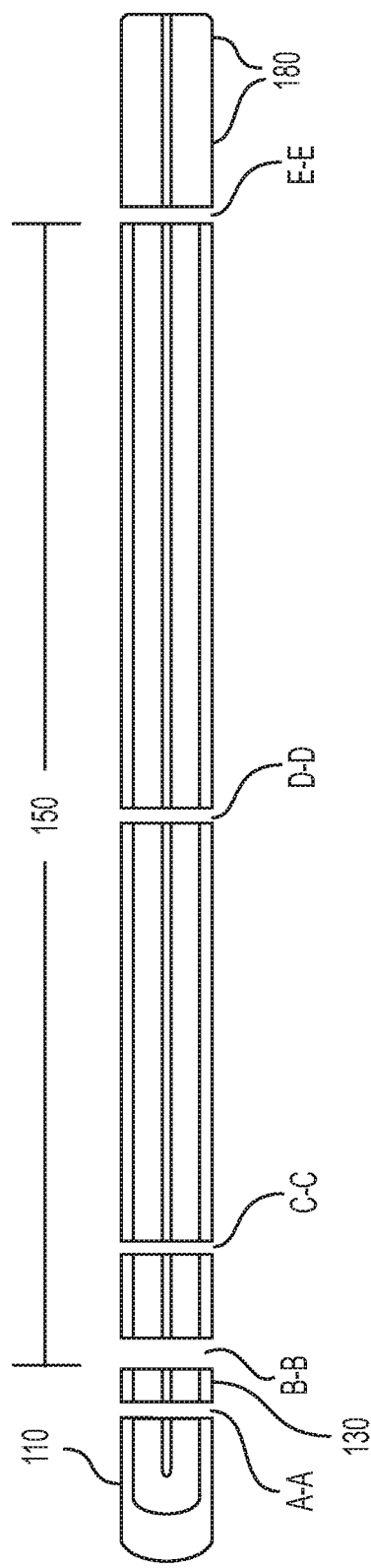
FIG. 2 is a cross-section taken along the longitudinal direction of the exemplary guidewire of FIG. 1.
Figure 3:
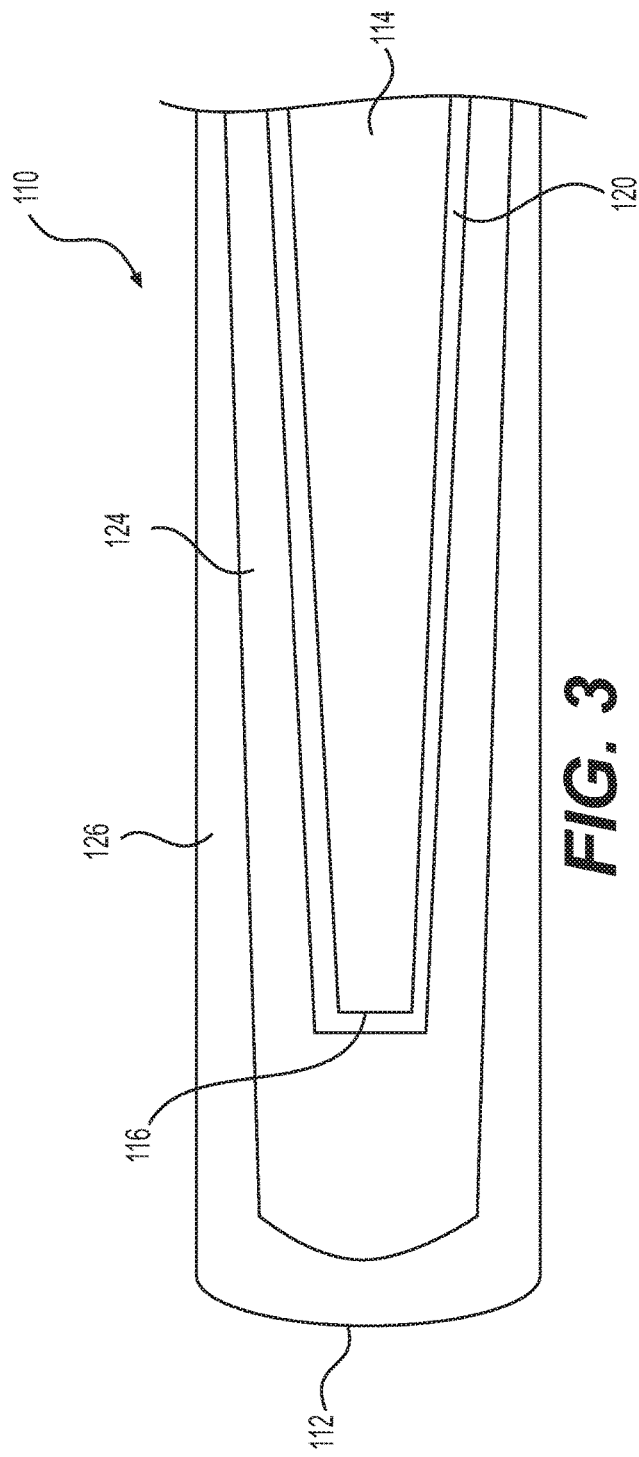
FIG. 3 is a longitudinal cross-sectional view of the first section of the exemplary guidewire of FIG. 1.
Figure 4:
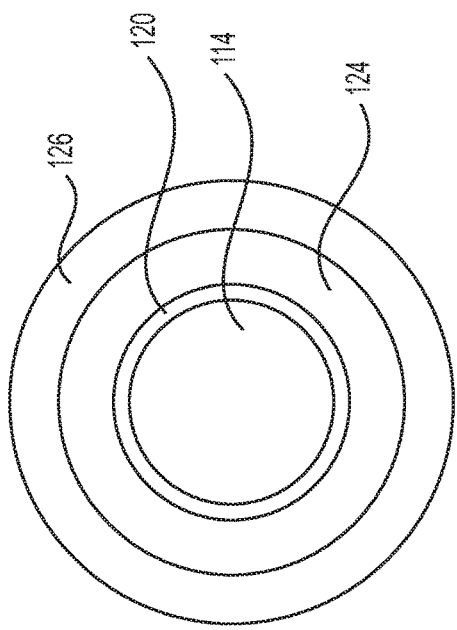
FIG. 4 is a radial cross-sectional view of the first section of the exemplary guidewire of FIG. 1, taken at line A-A.
Figure 5:
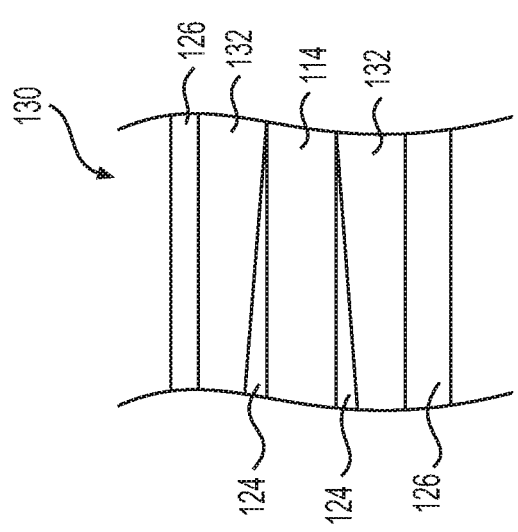
FIG. 5 is a longitudinal cross-sectional view of the second section of the exemplary guidewire of FIG. 1.
Figure 6:
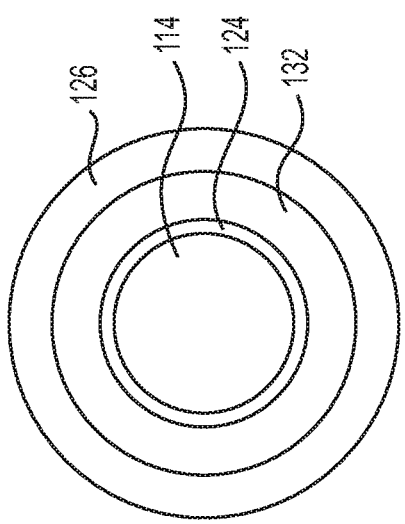
FIG. 6 is a radial cross-sectional view of the second section of the exemplary guidewire of FIG. 1, taken at line B-B.
Figure 7:
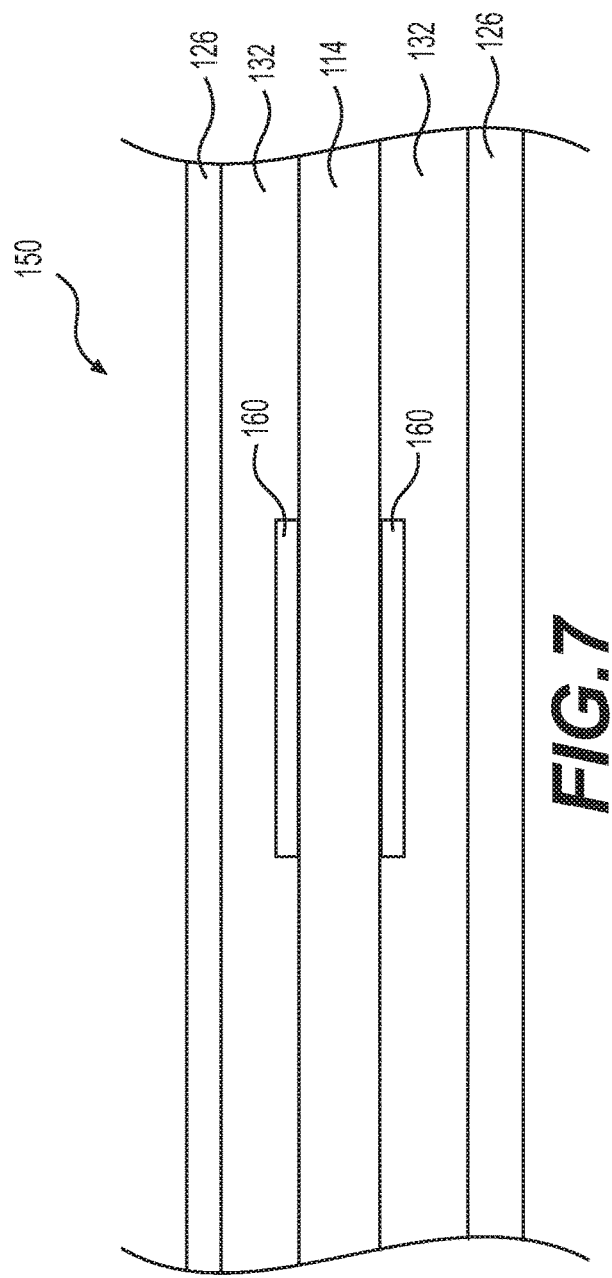
FIG. 7 is a longitudinal cross-sectional view of a portion of a third section of the exemplary guidewire of FIG. 1.
Figure 8:
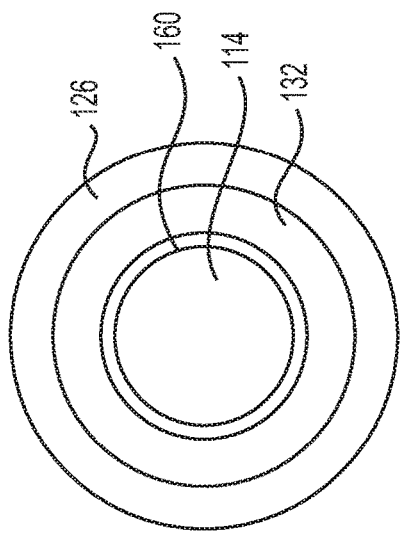
FIG. 8 is a radial cross-sectional view of a portion of the third section of the exemplary guidewire of FIG. 1, taken at line C-C.

Referencing FIGS. 1 and 2, a first exemplary guidewire 100 is configured for insertion into a bodily lumen such as, without limitation, a ureter. In this exemplary embodiment, the guidewire 100 may have an overall length of between ten to two hundred inches. For purposes of exemplary explanation only, the guidewire 100 will be described as having an overall length of approximately fifty-nine inches. The guidewire 100 may have a circular or rounded cross-sectional profile (i.e., axial profile) taken perpendicular to the dominant longitudinal dimension (i.e., the lengthwise dimension). By way of example, an outside diameter of the guidewire 100 may be between 0.025 to 0.10 inches, and more specifically range between 0.0345 and 0.0385 inches. For purposes of exemplary explanation only, the guidewire 100 will be described as having generally a circular axial profile with an outside diameter between approximately 0.035-0.038 inches. By way of example, the guidewire 100 may be comprised of differing layers and constituents along its length that may correspondingly change the cross-sectional make-up of the guidewire. As a result, the following discussion of the guidewire 100 constituents is broken down into a series of guidewire sections that are seamlessly coupled to one another between a distal tip (inserted first into the bodily lumen) and the proximal end.

Referring specifically to FIGS. 1-4, a first section 110 includes a distal tip 112 and a predetermined length extending proximally away from the tip. By way of example, the distal tip may comprise an atraumatic tip, though this is not a necessity. The first section 100 comprises a core 114 that may be solid or partially hollowed. In exemplary form, the core 114 comprises an alloy of nickel, titanium, and cobalt having a circular axial profile that need not be constant along the axial length of the first section 110. More specifically, the core 114 may taper in shape so that, in the case of a circular or rounded axial profile, the outside circumference of the core material decreases between the proximal portion of the first section 110 and the distal tip 112. By way of further example, the core 114 may have a circular axial profile that gradually tapers until reaching a blunt distal end 116, thereby embodying a frustoconical shape.

A second constituent of the first section 110 comprises a silane coating 120 applied over the exterior of the core 114 that is operative to encapsulate the distal end 116. In this exemplary embodiment, the core 114 may be dipped in liquid silane that cures to form the coating 120. Alternatively, the core 114 may be sprayed with a liquid silane that dries to form the coating 120. Those skilled in the art will understand the plethora of techniques that may be used to form a silane coating 120 over a core 114, with such techniques being omitted only in furtherance of brevity, and each of which shall fall within the scope of the instant disclosure. By way of example, the silane coating 120 may comprise any silane composition operative to promote adherence between the core 114 and a top coating 124.

By way of example, the top coating 124 may comprise a radiopaque thermoplastic polymer operative to encapsulate the distal end 116 of the core material, as well as the silane coating 120. By way of further example, the top coating 124 may comprise a polyester polycaprolactone based polyurethane elastomer such as, without limitation, tungsten loaded PELLETHANE, available from The Lubrizol Corporation. By making the top coating 124 radiopaque, the first section 110 is relatively impenetrable to the transmission of radiation, thus creating a clearly visible darkened image when within the field of view for X-ray, fluoroscopy, CT, or other radiation imaging technologies.

The top coating 124 is itself encapsulated by a surface coating 126. In exemplary form, the surface coating 126 may comprise a hydrophilic coating, where the distal end of the coating comprises the distal tip 112 of the guidewire. In exemplary form, the first section 110 may have a length of approximately two inches.

Referring to FIGS. 1, 2, 5, and 6, the first section 110 may be seamlessly bonded to a second section 130 that is operative to form a transition between a third section 150 and the first section 110. The second section 130 may include three of the same constituents as the first section 110, namely the core 114, the top coating 124, and the surface coating 126, in addition to a metal coil 132 positioned adjacent to the top coating 124. In exemplary form, the metal coil 132 provides micro ridges and valleys when covered by the top coating 124, which is operative to provide increased traction or a coefficient of friction greater than the first section. As will be discussed in more detail hereafter, a heat treatment may be applied to the guidewire 100 resulting in a portion of the top coating 124 diffusing beyond the first section 110 and into the second section 130 between the coil 132 turns and the core 114. In this fashion, post heat treatment, a thin portion of the top coating 124 sits atop and/or protrudes between the turns of the coil 132.

In this exemplary embodiment, the metal coil 132 may comprise stainless steel (such as a 304V alloy) or any other biologically inert/compatible or acceptable metal or metal alloy. The turns of the metal coil 132 may have a helical shape with an outer diameter substantially constant and ranging between 0.025 to 0.10 inches, and more specifically range between 0.0345 and 0.0385 inches. The metal comprising the turns of the coil 132 may have a circular, rounded, or other shaped cross-section. By way of example, the coil turns may have a square or rectangular cross-section. In other words, the metal wire comprising the coil 132, before it is coiled, may have a square or rectangular cross-section. In exemplary form, the second section 130 may have a length of approximately 0.2 inches.

Referencing FIGS. 1, 2, 7, and 8, post the second section 130 is the third section 150. This third section 150 may include the core 114 and, rather than having a silane coating 120 as in the first section 110, may include an epoxy primer coating 160 over top of the core 114 along a predetermined length of a distal portion and the proximal most portion. By way of example, this predetermined length may be 0.5 inches so that a distal portion has a 0.5 inch length epoxy primer coating 160 and the proximal most 0.5 inch length includes the epoxy primer coating 160 directly over the core 114. In exemplary form, the epoxy primer coating 160 may comprise a mixture of an epoxy resin, an epoxy polyamine adduct, and a glycidyl ester. The same metal coil 132 that may be present in the second section 130 may be present in the third section 150 and overlie the epoxy primer coating 160 (where present) and otherwise overlie and directly contact the core 114. The same surface coating 126 may be applied over the metal coil 132.

Figure 9:
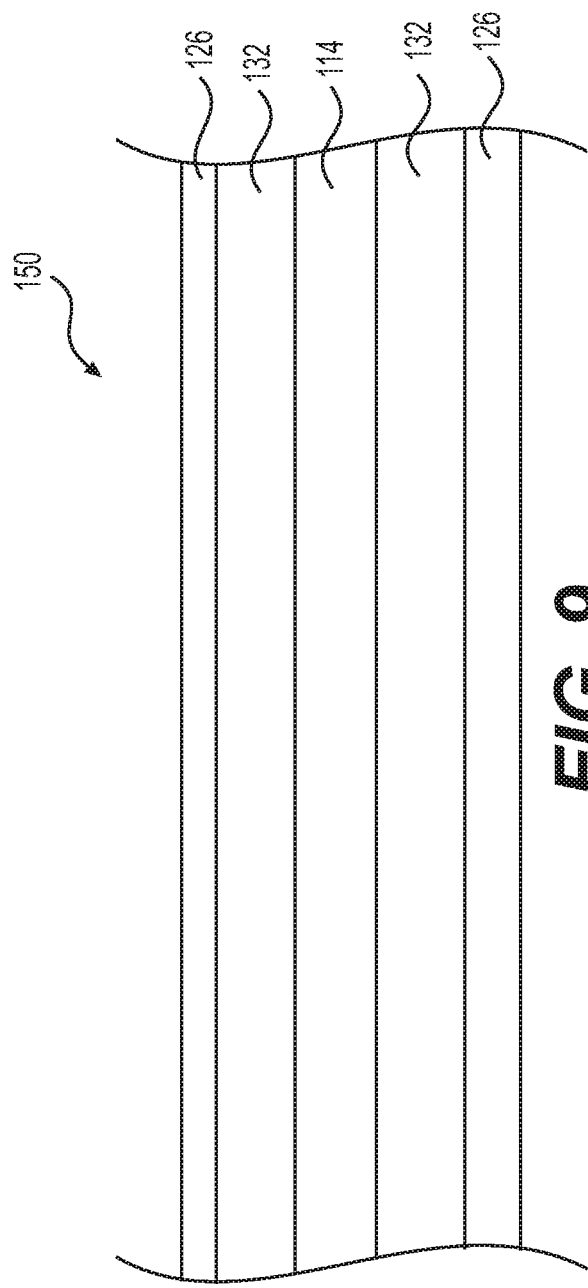
FIG. 9 is a longitudinal cross-sectional view of a portion of the third section of the exemplary guidewire of FIG. 1.
Figure 10:
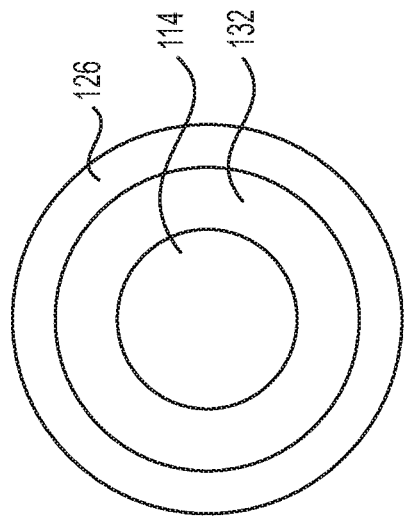
FIG. 10 is a radial cross-sectional view of the portion of the third section of the exemplary guidewire of FIG. 1, taken at line D-D.

Referencing FIGS. 9 and 10, the vast majority of the length of the third section 150 may omit the epoxy primer coating 160. In such a configuration, the core 114 is circumscribed by the metal coil 132, which itself is covered with the surface coating 126 to encapsulate the metal coil and core material. In this configuration, the metal coil 132 may be free floating over the core 114 thereby allowing the metal coil to move independent of the core 114. In exemplary form, the third section 150 may have a length of approximately 51 inches.

Referencing FIGS. 1, 2, 11, and 12, a fourth section 180 may seamlessly abut the third section 150 opposite the second section 130. This fourth section 180 may include the same core 114, yet omit the epoxy primer coating 160, the metal coil 132, and the surface coating 126. In exemplary form, the core 114 of this fourth section may include a hydrophobic coating 190. This hydrophobic coating 190 may comprise any number of hydrophobic materials such as, without limitation, polytetrafluoroethylene (PTFE). In exemplary form, the hydrophobic coating 190 may be applied in the form of a PTFE tube that is heat-shrinked to precisely circumscribe and contact the adjacent core 114. In this exemplary embodiment, the fourth section may have a length of 4.9 inches. By way of further example, the first section 110 has a lesser coefficient of friction than the second section 130, where the second section has a lesser coefficient of friction than the fourth section 180.

Figure 13:
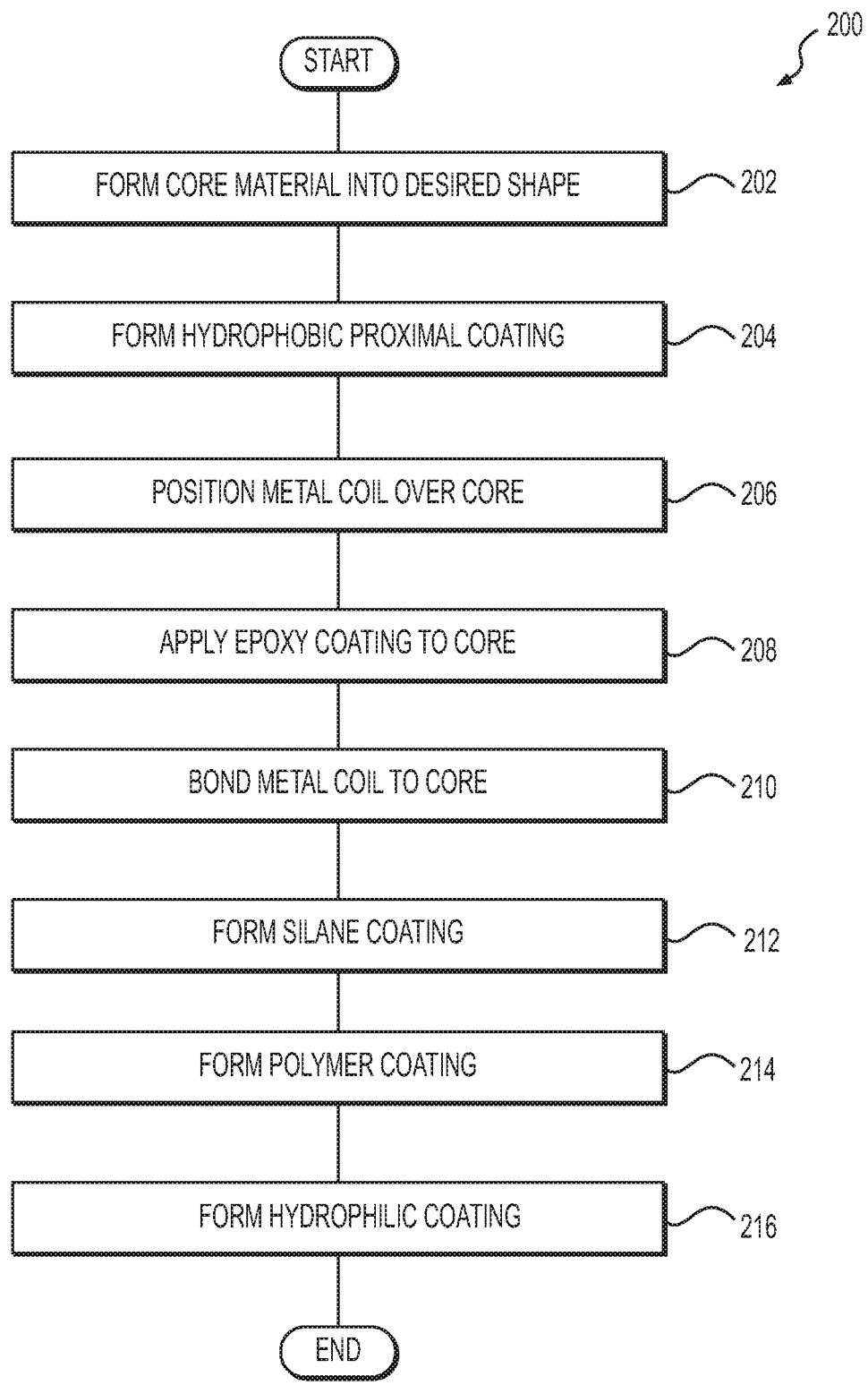
FIG. 13 is an exemplary process flow diagram for fabricating an exemplary guidewire in accordance with the instant disclosure.

Turning to FIG. 13, an exemplary process 200 for producing the exemplary guidewire 100 is provided. Specifically, fabrication of the foregoing guidewire 100 may commence at step 202 by forming the core 114 into a desired shape. By way of example, a predetermined length of core 114 (such as 59 inches), which length may vary depending upon the desired length of the guidewire, may be unwound from a spool of core material. The core 114 may have a generally uniform cross-section along its dominant longitudinal length that may be circular, oblong, or another shape. In exemplary form, the uniform cross-sections of the core may range between 0.015 and 0.090 inches in diameter and, more specifically, may range between 0.0240-0.0275 inches in diameter. This generally uniform cross-section may be supplemented by longitudinal lengths that are tapered or otherwise varied to change the overall width of the guidewire 100 and/or to change the proportion of the cross-section occupied by the core 114. By way of further example, the core 114 may comprise a cylindrical shape having a circular axial profile that is tapered along a predetermined length to provide a frustoconical tip. This tapering process may be part of step 202 and may be carried out by grinding or any other material removal process. In exemplary form, the tapering may occur on a 2 inch distal end of the core 114.

Post forming the core 114 into a desired shape in step 202, a subsequent step 204 may include formation of the hydrophobic coating 190 at a proximal end of the core material. Specifically, a hydrophobic tube of PTFE may be positioned to circumscribe a proximal section (or end) of the core 114. Post positioning of the PTFE tube around the core 114, heat is applied to the tube, which causes the tube to shrink and form fit to the exterior of the core 114, thereby providing a hydrophobic coating 190. In exemplary form, the resulting hydrophobic coating 190 may have a radial thickness ranging between 0.005 and 0.05 inches. More specifically, the hydrophobic coating may have a radial thickness of approximately 0.013 inches.

Before, during, or after formation of the hydrophobic coating 190 about the core 114, at step 206, the metal coil 132 is slid over a distal end of the core 114 until a proximal end of the metal coil abuts an intended or actual distal end of the hydrophobic coating 190. The length of the metal coil 132 may be chosen so that a distal section of the core 114 is not circumscribed by the coil. In exemplary form, the metal coil 132 may comprise any biocompatible metal or metal alloy including, without limitation, stainless steel 304V. It should also be known that the cross-section of each metal strand wound to form the coil may have a cross-sectional shape other than circular or oblong. For example, the metal strand may have a square or rectangular cross-sectional shape.

Before, during, or after positioning the metal coil 132 around the core 114, at step 208, an epoxy primer coating 160 is applied to predetermined portions of the core 114 to eventually interpose the core and metal coil. During step 208, an epoxy primer may be applied to a predetermined length of the core 114 (such as, without limitation, 0.5 inches) immediately distal to the intended or actual end location of the hydrophobic coating 190, as well as to a more distal location located about six inches (about 15 centimeters) from the distal tip of the core. Post application of the epoxy primer coating 160 and the metal coil 132, a heat treatment step 210 may be carried out to bond the metal coil 132 to the core 114 by curing the epoxy primer coating 160.

At step 212, a distal-most section (e.g., about two inches) of the core 114 may be dipped in a silane primer or have a silane primer spray applied thereto. Heat is applied to the wet silane composition post application to cure the silane and form a coating 120 over the distal core 114.

After the silane coating 120 is formed in step 212, a top coating step 214 may be carried out. In this step 214, a polymer coating 124 may be applied over the silane coating 120 by dipping or spraying a liquid polymer composition to the distal-most section (e.g., about two inches) of the core 114. Alternatively, the polymer coating 124 may be in the form of a tube wrapped in a disposable peel-away heat shrink tube, which are both applied over the silane coating 120. In exemplary form, the polymer composition may comprise a radiopaque material, when cured, such as, without limitation, tungsten loaded pellethane. Post application of the polymer coating 124 over the silane coating 120, a heat treatment may be carried to bond the polymer coating 124 to the silane coating 120 and core 114. During such a heat treatment, portions of the polymer coating 120 may flow into communication with and under the metal coil 132 and become entrained within the coils, thereby bonding the polymer coating 124 to the metal coil 132. Post heat treatment, in the context where a peel-away heat shrink tube is utilized, the disposable heat shrink tube may be peeled away to leave only the polymer coating 124 as the outermost surface of the guidewire 100.

At step 216, a hydrophilic surface coating 126 is applied over the complete length of the polymer top coating 124 and the metal coil 132, but need not be applied over the hydrophobic coating 190. Application of the hydrophilic surface coating and any resulting cure sub-steps may be fashioned to arrive at a guidewire with an atraumatic distal tip 112. In exemplary form, the hydrophilic surface coating may have a radial thickness of between 0.0001 and 0.001 inches and, more specifically have a radial thickness of approximately 0.0005 inches.

Figure 14:
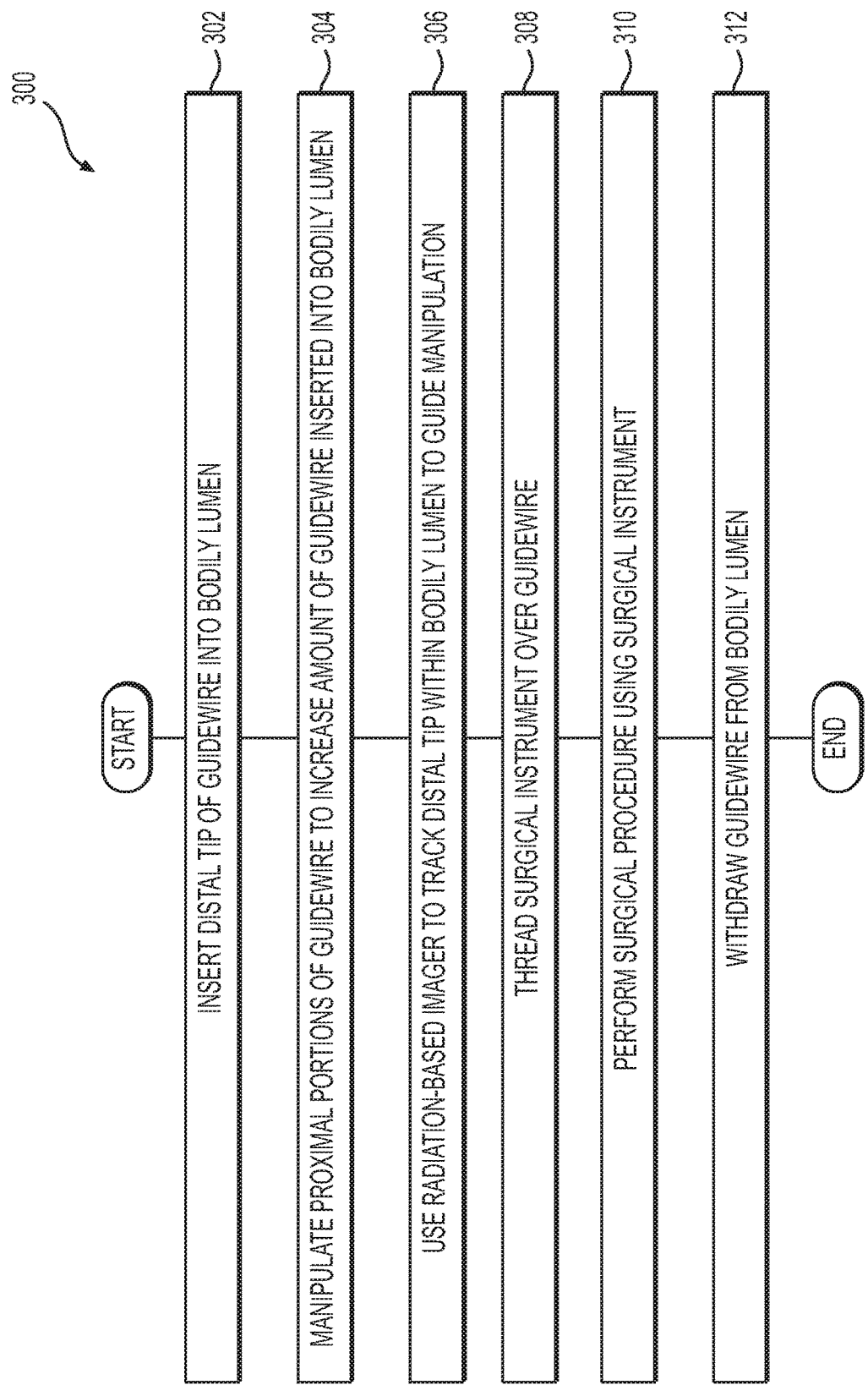
FIG. 14 is an exemplary process flow diagram for using an exemplary guidewire disclosed herein in accordance with the instant disclosure.

Turning to FIG. 14, an exemplary process 300 for using the exemplary guidewire 100 is disclosed. Specifically, the distal tip 112 may be inserted at step 302 into the bodily lumen of a mammal. Post insertion of the distal tip 112, an operator of the guidewire 100 may twist and manipulate the guidewire at step 304 to force more of the guidewire deeper into the bodily lumen until the distal tip reaches a desired position within the bodily lumen. As part of twisting and manipulating the guidewire, a fluoroscopic unit (known to those skilled in the art) may be utilized by the operator at step 306 to provide visual indications of the location of the distal tip 112 relative to the bodily lumen.

As discussed previously, the first section 110 of the guidewire 100 includes a radiopaque polymer coating 124 (e.g., tungsten loaded pellethane) that, under fluoroscopy or other radiation-based imager, shows up as a darkly shaded object contrasting against the lighter shades of the bodily lumen. Consequently, the operator of the guidewire 100 can redirect the guidewire in real-time responsive to real-time images generated from a radiation-based imager. This same imager may be used by the operator to identify an appropriate termination location for the distal tip. Upon reaching the appropriate termination location for the distal tip within the bodily lumen, the operator may move to step 308 to thread the appropriate surgical instrument over the guidewire 100.

In exemplary form, the surgical instrument threaded over the guidewire 100 may vary greatly depending upon the bodily lumen the guidewire is located within as well as the intended surgical procedure. Consequently, any surgical device that may be threaded over a guidewire is implicated herein and within the scope of the intended use of being threaded over the instant guidewire 100. By way of example, in the context of the bodily lumen comprising a ureter, the surgical instrument may comprise a ureteroscope. By way of further example, in the context of the bodily lumen comprising a ureter, the surgical instrument may comprise at least one of a ureteral stent and a ureteral access sheath. It should be understood that the exemplary guidewire 100 is not limited to urinary applications. Instead, the exemplary guidewire 100 may be used in circulatory procedures including, without limitation, angioplasty procedures. It should be noted that contrary to conventional wisdom, the hydrophilic surface coating 126 provides a lower coefficient of friction for sliding surgical instruments thereover than a comparable hydrophobic coating.

Before, during, or post the surgical procedure, an operator of the guidewire 100 may pull or otherwise withdraw the guidewire through the bodily lumen including withdrawal of the distal tip 112 from the bodily lumen at step 312.

It should also be noted that the exemplary guidewire 100 may be disposable or may be used repeatedly for the same or different surgical procedures.

Following from the above description, it should be apparent to those of ordinary skill in the art that, while the methods and apparatuses herein described constitute exemplary embodiments of the present invention, the invention described herein is not limited to any precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A guidewire comprising:
a hydrophilic surface coating encasing a metal coil and a majority length of a core to form a distal closed tip, the metal coil circumscribing the core along a predetermined length, the core extending longitudinally beyond the metal coil in both a proximal direction and a distal direction, wherein a proximal section of the guidewire includes a hydrophobic surface coating over a minority length of the core.

2. The guidewire of claim 1, wherein at least a portion of the core extending in the distal direction beyond the metal coil includes a silane coating.

3. The guidewire of claim 2, wherein the silane coating is separated from the hydrophilic surface coating by a thermoplastic polymer layer.

4. The guidewire of claim 3, wherein the thermoplastic polymer layer is radiopaque.

5. The guidewire of claim 4, wherein the thermoplastic polymer layer comprises a polycaprolactone based polyurethane elastomer.

6. The guidewire of claim 5, wherein the polycaprolactone based polyurethane elastomer comprise tungsten loaded pellethane.

7. The guidewire of claim 1, wherein the core includes a frustroconical shape that extends beyond the metal coil in the distal direction.

8. The guidewire of claim 1, wherein the core is coated in an epoxy primer.

9. The guidewire of claim 8, wherein the epoxy primer comprises a mixture of an epoxy resin, an epoxy polyamine adduct, and a glycidyl ester.

10. The guidewire of claim 8, wherein the epoxy primer is adjacent the hydrophobic surface coating.

11. The guidewire of claim 1, wherein an overall length of the guidewire is between ten and two hundred inches.

12. The guidewire of claim 1, wherein the core has a median diameter between approximately 0.035 inches and 0.038 inches.

13. The guidewire of claim 1, wherein the distal closed tip is atraumatic.

14. The guidewire of claim 1, wherein the core is at least one of solid and hollowed.

15. The guidewire of claim 1, wherein the core comprises an alloy of nickel, titanium, and cobalt.

16. The guidewire of claim 1, wherein the core includes a cross-sectional shape comprising at least one of circular, oblong, and rectangular.

17. The guidewire of claim 1, wherein the core includes a tapered section.

18. The guidewire of claim 1, wherein the core includes a frustroconical section.

19. The guidewire of claim 1, further comprising a silane coating interposing the core and the hydrophilic surface coating.

20. The guidewire of claim 19, wherein the silane coating is spaced from the hydrophilic surface coating by a thermoplastic polymer layer.

21. The guidewire of claim 20, wherein the thermoplastic polymer layer is radiopaque.

22. The guidewire of claim 21, wherein the thermoplastic polymer layer comprises a polycaprolactone based polyurethane elastomer.

23. The guidewire of claim 22, wherein the polycaprolactone based polyurethane elastomer comprise tungsten loaded pellethane.

24. The guidewire of claim 1, wherein the core is coated in an epoxy primer in the form of two ring-shaped coatings spaced apart from one another.

25. The guidewire of claim 24, wherein each of the two ring-shaped coatings is no greater than ten inches in length.

26. The guidewire of claim 1, wherein the metal coil comprises stainless steel.

27. The guidewire of claim 1, wherein the metal coil has a radial cross-section that is rectangular in shape.

28. A method of fabricating a guidewire comprising:
mounting a metal coil over a core so that the metal coil circumscribes the core along a predetermined length, the core extending longitudinally beyond the metal coil in both a proximal direction and a distal direction;
encasing the metal coil and a majority length of the core in a hydrophilic exterior surface layer so a distal tip of the guidewire is closed; and,
forming a hydrophobic exterior surface over a minority length of the core.

29. The method of claim 28, further comprising shaping the core to create a tapered distal segment.

30. The method of claim 29, wherein shaping the core to create the tapered distal segment include grinding the core to remove material from the core.

31. The method of claim 28, wherein forming the hydrophobic exterior surface over the minority of the core includes heat shrinking a hydrophobic tube over the minority of the core.

32. The method of claim 31, wherein the hydrophobic tube is heat shrinked over a proximal-most section of the core.

33. The method of claim 31, wherein the hydrophobic tube comprises polytetrafluoroethylene.

34. The method of claim 28, further comprising applying an epoxy primer to the core so as to interpose the core and metal coil.

35. The method of claim 34, wherein the epoxy primer is applied to form two rings around the core that are spaced apart from one another.

36. The method of claim 34, further comprising heat treating the applied epoxy primer to bond the core to the metal coil where the epoxy primer was applied.

37. The method of claim 28, further comprising applying a silane primer to a distal most portion of the core.

38. The method of claim 37, further comprising curing the applied silane primer via a heat treatment.

39. The method of claim 37, wherein encasing the metal coil and a majority of the core in the hydrophilic coating also includes encasing the silane primer.

* * * * *